United States Patent [19]

Conway et al.

[11] E Patent Number: Re. 33,206

[45] Reissued Date of Patent: May 1, 1990

[54] MALE CONDOM CATHETER HAVING ADHESIVE ON ROLLED PORTION

[75] Inventors: James A. Conway; Peter R. Conway; Philip J. Conway, all of Chatfield, Minn.

[73] Assignee: Mentor Corporation, Goleta, Calif.

[21] Appl. No.: 917,145

[22] Filed: Oct. 9, 1986

Related U.S. Patent Documents

Reissue of:

[64] Patent No.: 4,475,910
Issued: Oct. 9, 1984
Appl. No.: 307,792
Filed: Oct. 2, 1981

[51] Int. Cl.[5] ..... A61E 5/44

[52] U.S. Cl. ..... 604/349; 128/844

[58] Field of Search ..... 428/36, 343, 352; 285/260; 138/109, 285; 604/347, 349, 350, 351, 352; 128/760, DIG. 21, 137 R, 157

[56] References Cited

U.S. PATENT DOCUMENTS

| | | | |
|---|---|---|---|
| 2,389,831 | 11/1945 | Welsh | 604/352 |
| 3,403,682 | 10/1968 | McDonell | 604/352 |
| 3,520,305 | 7/1970 | Davis | 604/349 |
| 3,739,783 | 6/1973 | Broerman | 604/349 |
| 3,788,324 | 1/1974 | Lim . | |
| 3,835,857 | 9/1974 | Rogers et al. | 604/349 |
| 4,187,851 | 2/1980 | Hauser | 604/352 |
| 4,284,079 | 8/1981 | Adair . | |
| 4,339,485 | 7/1982 | Shibano et al. | 156/334 |

OTHER PUBLICATIONS

"The Silicones as Tools in Biological Engineering", Braley, Med. Electron. Biol. Engng., vol. 3 Pergamon Press, Great Britain, 1965 (pp. 127–136).

*Primary Examiner*—J. L. Kruter
*Attorney, Agent, or Firm*—Kinney & Lange

[57] ABSTRACT

A male urinal device (10) is disclosed. Device (10) includes a laminated sheath (14) having an inner layer (26) of latex rubber and outer layer (28) of silicone rubber. Adhesive (24) is stored between the inner and outer layers (26, 28) when sheath (14) is rolled. As sheath (14) is unrolled, adhesive (24) is released from outer layer (28) and adheres to inner layer (26). Upon pressing sheath (14) to a penis (12), a leak-free bond is created.

8 Claims, 5 Drawing Sheets

FIG. 1
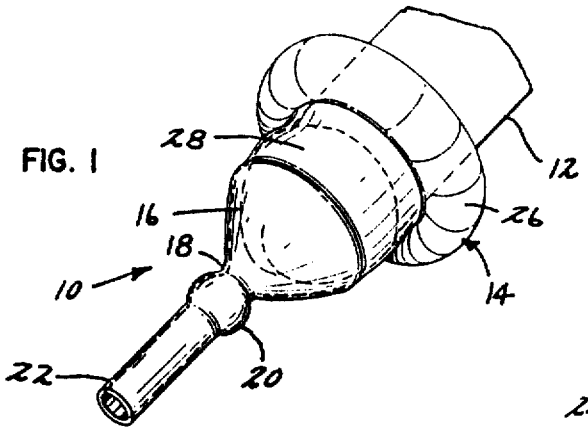
FIG. 2
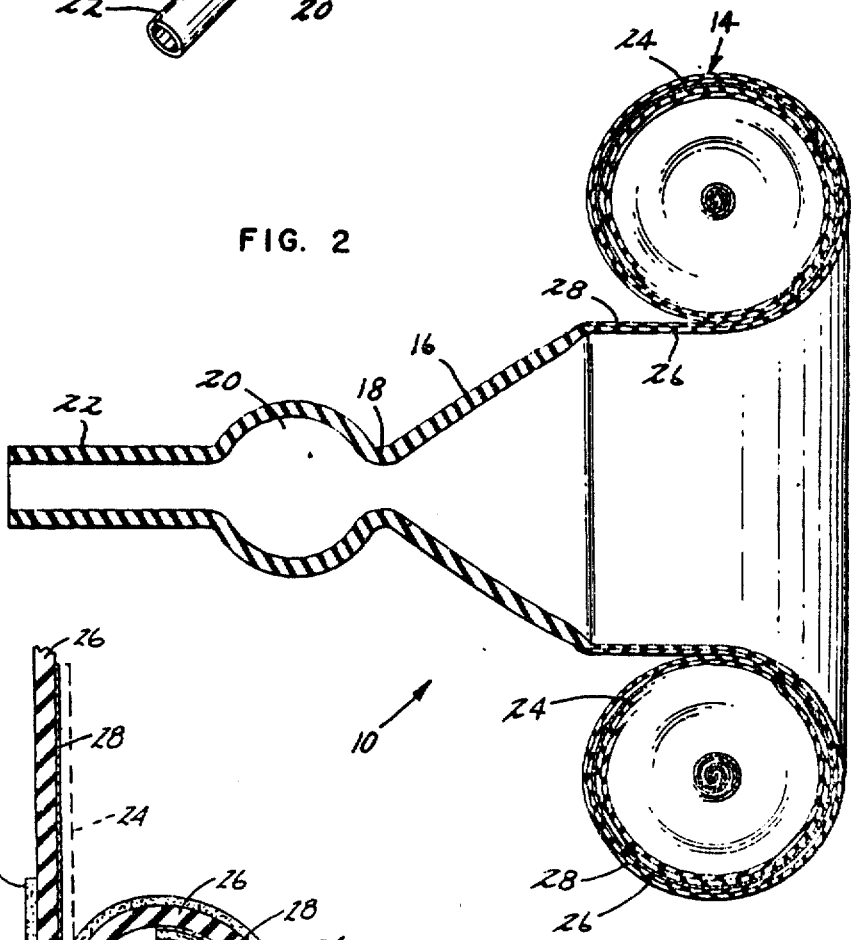
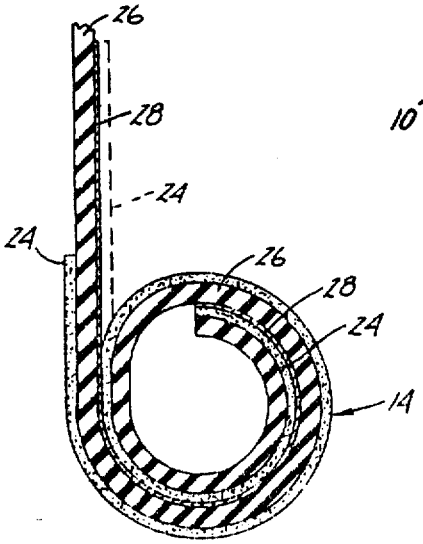
FIG. 5

MALE CONDOM CATHETER HAVING ADHESIVE ON ROLLED PORTION

Matter enclosed in heavy brackets [ ] appears in the original patent but forms no part of this reissue specification; matter printed in italics indicates the additions made by reissue.

TECHNICAL FIELD

This invention relates to a male urinal device and, more particularly, to an external male catheter for catching and removing to a collection device unrestrained urine discharges.

BACKGROUND OF THE INVENTION

In connection with a male urinal device of the type using a urine receptical worn on the body or near the body, it is common to use a sheath of flexible material placed over the penis and connected to the receptical with a tube or other form of flexible conduit. Some devices customarily include a narrow tape wound relatively tightly about the sheath to hold the sheath securely and prevent leakage. Since urinal devices must be worn for long periods of time, particularly in the case of paraplegics, wound tape exerts continuous pressure on a penis and particularly on the urethral passage which is located on the under side of the penis fairly close to the surface. Constrictions and discomfort may result. It is not uncommon for a tightly wound tape to cause swelling or even gangrene. On the other hand, a loose tape can allow leakage of urine and resultant irritation.

In U.S. Pat. No. 3,863,638, Rogers shows a liner pad between the sheath and the penis to form a cushion and absorb some of the pressure exerted by an externally wound tape. Often, however, the pad is inadvertently not used by an attendant applying the device to a patient or the pad is simply too wide or too narrow for a particular penis. Additionally, Rogers indicates the use of adhesive on both sides of the pad, thus eliminating the need for an external tape.

In U.S. Pat. No. 4,187,851, [Houser] *Hauser* also eliminates an external tape by showing the use of an adhesive on both the inner and outer surfaces of a pad. In this way, the pad can be wound around a penis, and the sheath of the urinal device rolled over the pad and held in place by the adhesive. Although the devices of Rogers and [Houser] *Hauser* eliminate externally wound tape, they continue to present the problems which result whenever a material is too tightly wound about a penis.

Broerman in U.S. Pat. No. 3,739,783 shows a urinal device to be used without wound tape or pads. An adhesive is painted onto a penis and a sheath impregnated with silicone rubber placed over the adhesive. The method and device, however, are not satisfactory since reliability continues to depend on an attendant's use of a proper adhesive and proper application of the adhesive.

Hence, there continues to be a need for a safe, leak-free male urinal device.

SUMMARY OF THE INVENTION

In one embodiment, a male urinal device in accordance with the present invention includes a condom means for fitting about a normal, flaccid penis. The condom means joins catheter means for carrying urine to collection means. The condom means includes a flexibly cylindrical member rolled outwardly upon itself forming consecutively larger rolls. The member has adhesive between consecutive rolls. The member includes outer means for releasing the adhesive when the member is unrolled and inner base means for providing an adhesive adhering surface when the member is unrolled. In this fashion, the device may be stored with the adhesive protected between consecutive rolls of the member and used by unrolling the member onto a penis allowing the adhesive to release from the outer releasing means and adhere to the base means and the penis.

In a preferred embodiment, the male urinal device is in the form of an external male catheter having a sheath or sleeve for fitment about a normal, flaccid penis. The sleeve has an open end and an end opposite which unitarily joins a bulbous surge chamber and a catheter portion for connection to a tube leading to a collection receptacle. The sleeve is comprised of an internal layer of latex rubber with an external layer of an adhesive release agent. In a pre-operational position, the sleeve is outwardly rolled upon itself. A pressure-sensitive, medical adhesive is located between consecutive rolls. When the sleeve is rolled onto a penis, the adhesive adheres to the latex rubber layer and releases from the release agent layer. In this way, the adhesive is sandwiched between the latex rubber and the penis and upon applying a one time appropriate amount of pressure to the sleeve and penis forms a leak-free bond.

Thus, the method for installing the male external catheter onto a penis includes the steps of unrolling the sleeve or condom portion of the catheter onto the penis and pressing the unrolled condom portion against the penis to form completely around the penis a bond between the condom portion and the penis. As indicated the adhesive is released from the outer surface of the condom portion and adheres to the inner surface of the condom portion during the unrolling step.

The present invention includes a method for making a male urinal device. The method is comprised of dipping a male-type form of the device into a liquid-state base material, curing the base material adhering to the dipped form, applying a liquid-state release material to the sheath portion of the cured base material, curing the release material, applying a pressure-sensitive adhesive to a cylindrical portion of the cured release material, and rolling from an end of a form the sheath portion of the device.

The present device is particularly advantageous in that it eliminates all need for a wound tape or pad about the penis. Consequently, the medical risk of swelling and gangreen is eliminated. Additionally, the present device eliminates the need for an attendant to prepare the surface of the penis with a proper adhesive. The present device provides a mechanism for storing a proper adhesive in a pre-operational position and for automatically transferring the adhesive to the required surface for making the appropriate bond between the penis and the urinal device.

The device is easily installed on a penis by simply unrolling and pressing. Additional steps of applying an adhesive or applying a tape or a pad have been eliminated.

These and other advantages obtained by the use of the present invention may be better understood by reference to the drawings which form a further part hereof and to the accompanying descriptive matter in which there is illustrated and described preferred and other embodiments of the invention.

BRIEF DESCRIPTION OF THE DRAWINGS

FIG. 1 is perspective view of a urinal device being installed on a penis in accordance with the present invention;

FIG. 2 is a cross-sectional view of a device in the pre-operational position;

FIG. 5 is a cross-sectional view of a portion of the device shown in FIG. 2 on a larger scale and with the device partially unrolled to show the transfer of the adhesive from the outer to the inner surfaces of the catheter.

DETAILED DESCRIPTION OF THE INVENTION

Figure 3:
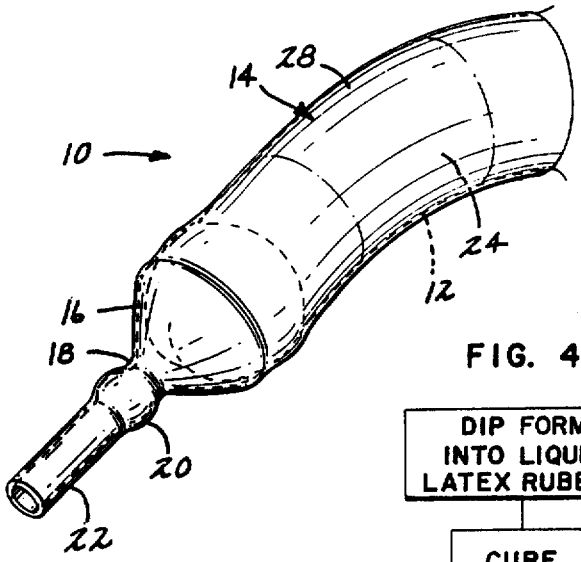
FIG. 3 is a perspective view of a device installed on a penis.

Referring now to the drawings wherein like reference numerals designate identical or corresponding parts throughout the several views, and more particularly to FIG. 1, a male urinal device in accordance with the present invention is designated generally as 10. Device 10 is shown as an external catheter installed about a male penis 12. Device 10 is comprised of a condom portion in the form of a sheath or sleeve 14, merging with a conical portion 16 to a constriction 18 before opening into a bulbous, surge chamber 20 which connects with a catheter or tube portion 22. Surge chamber 20 also serves as an anti-kink mechanism for tube 22 and a backflow prevention device. Device 10 requires a sheath 14, but may, of course, have more or less of the other indicated elements, and such elements may assume various shapes or be arranged in an order other than that illustrated.

Sheath 14 is cylindrical and has sufficient length to provide an adequate cylindrical contact surface for adhesive 24 explained more fully hereinafter. Sheath 14 is comprised of layers of material. An inner layer 26 is a base material which unitarily connects with conical portion 16, surge chamber 20 and catheter tube 22. Inner layer 26 of sheath 14 has a relatively thin cross sectional thickness as compared with the thickness of conical portions 16, surge chamber 20 and tube 22. The latter, thicker elements must generally retain their indicated shapes without being supported by internal or external structure. Sheath 14 fits about a penis 12 and, consequently, assumes the shape of the penis.

An outer layer 28 is laminated or otherwise applied to inner layer 26. It is understood, of course, that intervening layers may exist, but do not have particular significance with respect to the present invention. Outer layer 28 also has a relatively thin cross section. Outer layer 28 preferably extends the entire length of sheath 14.

With sheath 14 rolled in a pre-operational position, adhesive 24 is located between the outer surface of outer layer 28 and the inner surface of inner layer 26 of one or more consecutive rolls. The inner layer 26 provides an inwardly facing surface to which adhesive 24 readily adheres. The outer layer 28 provides a surface facing outwardly from which adhesive 24 is readily released.

Inner layer 26 of sheath 14, conical portion 16, surge chamber 20 and tube 22 are formed from a latex rubber or other suitable base material, such as a synthetic rubber. The outer layer 28 is a silicone rubber or other suitable adhesive release material. Outer layer 28 is preferably not porous since adhesive release is less complete. The adhesive 24 is a medically approved, pressure-sensitive adhesive suitable for creating a bond between human skin and the base material. The adhesive bond must be sufficiently strong and resistant to moisture to prevent urine leakage therethrough, while not being so strong as to cause pain when device 10 is removed from a penis.

Figure 4:
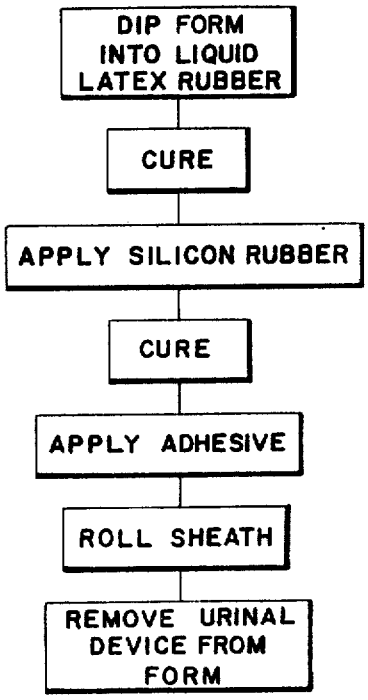
FIG. 4 is a flow diagram indicating the method for making the male urinal device in accordance with this invention.

As indicated in FIG. 4, urinal device 10 is made by using a male-type form (not shown) having an outer contour similar to the inner contour of a device 10. The form is dipped into a liquid-state base material. When removed, the base material adhering to the dipped form is cured in order to form inner layer 26 of sheath 14 as well as conical portion 16, surge chamber 20 and tube 22. The form may be dipped and cured multiple times. The base material portion of device 10 may be removed from the first form and placed on a second form or not. Next, a liquid-state release material, like silicone rubber, is applied to the sheath portion of the cured base material. The release material is allowed to cure to create outer layer 28 of sheath 14. Device. 10 again may or may not be removed from one form and placed on another. The pressure-sensitive adhesive 24 is then applied to a cylindrical portion of the outer surface of outer layer 28. Sheath 14 is rolled from its open end outwardly upon itself toward conical portion 16. Device 10 is then easily stretched and removed from the male-type form and is in its pre-operational position ready to be packaged or used.

To use urinal device 10, conical portion 16 is brought into proximity with the tip of a penis 12 as shown in FIG. 1. Sheath 14 is unrolled onto the penis. As unrolling occurs, as best shown in FIG. 5, adhesive 24 is released from the release material of outer layer 28 and adheres to the base material of inner layer 26. To show this more clearly, the adhesive 24 is shown in dotted lines on the portion of the outer surface 28 which has been unrolled to show that the adhesive has been released from this outer surface. Hence, when sheath 14 is completely unrolled, there is no adhesive along outer layer 28. Rather, the adhesive is located on the inner surface of inner layer 26. By pressing a cylindrical portion of the extended sheath 14 against the penis, a bond between the sheath and the penis is formed to hold device 10 safely in place in a leak-free fashion, as shown in FIG. 3. At the end of device 10 opposite sheath 14, a delivery tube (not shown) is connected with tube 22 to conduct urine to a containing receptacle (not shown).

Device 10 is removed from a penis by reversing the hereinbefore indicated steps.

Thus, the foregoing description has given numerous characteristics and advantages of the present invention, together with details of structure and function. It is to be understood, however, as indicated a number of times hereinbefore, that the disclosure is illustrative only. Consequently, any changes made, especially in matters of shape, size and arrangement, to the full extent extended by the general meaning of the terms in which the appended claims are expressed, are within the principle of the invention.

What is claimed is:

1. A male condom catheter designed to be connected to a urine collection means and comprising a thin cylindrical sheath member of resilient material rolled outwardly upon itself to form consecutively larger rolls, said sheath member having an outer surface and an inner surface designed to engage a penis when the catheter is unrolled, and the outer surface of the sheath member having prior to the rolling thereof a layer of pressure sensitive adhesive over a substantial portion thereof with a release layer between said adhesive and the outer surface of the sheath member so that as the sheath member is rolled up the pressure sensitive adhesive on the outer surface is in direct contact with the inner surface of an adjacent roll so that as the sheath member is unrolled the adhesive on the outer surface is transferred to the porton of the inner surface in engagement with the outer surface, without rolling the catheter inside out, to cause the inner surface to adhere to the penis over which the sheath is placed.

2. A device in accordance with claim 1 wherein said release layer is a silicon rubber layer of material.

3. The male condom catheter of claim 1 in which the thin sheath member has an integral conical portion of thicker material which is designed to be connected to a urine collection means.

4. The male condom catheter of claim 1 in which the adhesive is between the inner and outer surfaces of one or more consecutive rolls so that the adhesive is covered by the inner surface when the sheath is in rolled up condition.

[5. The method of applying a male condom catheter to a penis comprising:

forming a thin cylindrical sheath member of resilient material, said sheath member having an outer surface and an inner surface designed to engage a penis, and the outer surface of the sheath member having a layer of pressure sensitive adhesive over a substantial portion thereof with a release layer between said adhesive and the outer surface of the sheath member;

rolling said sheath member outwardly upon itself to form consecutively larger rolls so that the pressure sensitive adhesive on the outer surface is in direct contact with the inner surface of an adjacent roll;

unrolling the sheath member onto the penis so that the adhesive is transferred to the portion of the inner surface which was in engagement with the outer surface in the rolled up condition; and pressing said unrolled sheath member against the penis to cause the adhesive to adhere to the penis to form a bond between the sheath member and the penis.]

*6. A male condom catheter to be adhesively secured to a penis and designed to be connected to a urine collection means, said catheter comprising a thin, flexible cylindrical member of resilient material rolled outwardly upon itself to form a single roll with consecutively larger turns, the outer surface of the cylindrical member having an adhesive release layer thereon and said turns having a layer of pressure sensitive adhesive therebetween in contact with the inner surface of the cylindrical member and in contact with the release layer so that upon said cylindrical member being unrolled onto a penis, the adhesive releases from the adhesive release layer due to the unrolling of the cylindrical member and adheres only to the inner surface of the cylindrical member to cause the cylindrical member to adhere to the penis.*

*7. The catheter of claim 6 in which the adhesive release layer and the adhesive extend over at least one turn of the roll.*

*8. The catheter of claim 6 in which there is a bulbous surge chamber secured to the outlet side of the cylindrical member.*

*9. The catheter of claim 6 in which the adhesive release layer is formed of silicon rubber.*

* * * * *